United States Patent
Granger, Jr. et al.

[11] Patent Number: 5,903,147
[45] Date of Patent: May 11, 1999

[54] EDDY CURRENT ARRAY INSPECTION DEVICE FOR SHAPED HOLES

[75] Inventors: Carl Granger, Jr., West Chester, Janice L. Granger, executrix; Francis H. Little, Cincinnati, both of Ohio; Thomas B. Hewton, Cape Coral, Fla.; Kristina H. V. Hedengren, Schenectady, N.Y.

[73] Assignee: General Electric Company, Cincinnati, Ohio

[21] Appl. No.: 08/819,833

[22] Filed: Mar. 18, 1997

[51] Int. Cl.$^6$ ............................ G01N 27/72; G01N 27/82; G01R 33/12
[52] U.S. Cl. .............................. 324/219; 324/262; 33/302
[58] Field of Search ...................... 324/219, 220, 324/221, 262, 242; 33/302, 542, 544.4; 73/866.5

[56] References Cited

U.S. PATENT DOCUMENTS

| | | |
|---|---|---|
| 2,622,125 | 12/1952 | Bender . |
| 2,622,126 | 12/1952 | Bender . |
| 4,797,613 | 1/1989 | Wentzell . |
| 5,182,513 | 1/1993 | Young et al. . |
| 5,237,271 | 8/1993 | Hedengren . |
| 5,262,722 | 11/1993 | Hedengren et al. . |
| 5,315,234 | 5/1994 | Sutton, Jr. et al. . |
| 5,389,876 | 2/1995 | Hedengren et al. . |
| 5,442,286 | 8/1995 | Sutton, Jr. et al. . |
| 5,452,182 | 9/1995 | Eichelberger et al. . |
| 5,465,045 | 11/1995 | DeRock . |

Primary Examiner—Walter E. Snow
Attorney, Agent, or Firm—Andrew C. Hess; Nathan D. Herkamp

[57] ABSTRACT

An eddy current device for inspecting a component, such as a closed surface area of a gas turbine engine or the like, includes an eddy current array circuit having an active face for positioning on a surface portion of the component during an inspection operation and backing on a surface of the eddy current array circuit opposite to the active face. The eddy current array circuit and backing are disposed over the operating face and expandable sides of an extendible pin. The extendible pin has a slot formed therein with interior side edges which narrow toward the operating face of the pin at a predetermined slope. The expanding pin is positioned to cause the angled sides to mate while engaging the interior angled sides of the round or shaped hole to cause the exterior sides of the expandable pin to expand outwardly a greater distance as the pin is pushed deeper into the hole. This causes the eddy current circuit to conform with the shape of the surface to be inspected. The array sensor is so shaped that it can cover the closed surface in as little as one scan.

6 Claims, 3 Drawing Sheets

EDDY CURRENT ARRAY INSPECTION DEVICE FOR SHAPED HOLES

RELATED APPLICATIONS

The present application is related to the following patents:

Patent application Ser. No. 07/696,455, issued as U.S. Pat. No. 5,389,876, entitled "Eddy Current Probe Arrays" by Kristina H. Hedengren et al., which discloses and claims a plurality of spatially correlated eddy current probe elements sufficiently disposed within a flexible interconnecting structure to collect a discrete plurality of spatially correlated eddy current measurements for nondestructive near surface flaw detection. This patent is assigned to the same assignee as the present application and is incorporated herein in its entirety by reference.

Patent application Ser. No. 07/696,456, issued as U.S. Pat. No. 5,182,513, entitled Method and Apparatus for a Multi-Channel Multi-Frequency Data Acquisition System for Nondestructive Eddy Current Inspection Testing by John D. Young et al., which discloses and claims a method and apparatus for acquiring a plurality of synchronized, spatially correlated, discrete eddy current measurement signals for image processing. This patent is also assigned to the same assignee as the present application and is incorporated herein by reference in its entirety.

Patent application Ser. No. 07/696,457, issued as U.S. Pat. No. 5,237,271, entitled Apparatus and Method for Non-Destructive Testing Using Multi-Frequency Eddy Currents by Kristina H. Hedengren, which discloses and claims a method for improving resolution and characterization in detection of near surface flaws using non-destructive eddy current inspection. This patent is also assigned to the same assignee as the present application and is incorporated herein by reference in its entirety.

U.S. Pat. No. 5,452,182, entitled "A Flexible High Density Interconnect Structure and Flexibly Interconnected System" by Charles W. Eichelberger, et al., which describes a multi-layer multi-component integrated fabrication technology suitable for making flexible, spatially correlated, eddy current probe arrays for inspecting surfaces which have complex geometric shapes. This patent is also assigned to the same assignee as the present application and is incorporated herein by reference in its entirety.

Patent application Ser. No. 07/862,699, issued as U.S. Pat. No. 5,262,722, entitled An Apparatus for Near Surface, Nondestructive Eddy Current Scanning of a Conductive Part Using a Multi-Layer Eddy Current Probe Array by Kristina H. Hedengren, et al., which describes an ultra-thin, flexible, film-like, multi-layer eddy current probe array structure which is configured to provide electrical and mechanical interconnection to respective system electronics and mechanical scanning means. This patent is also assigned to the same assignee as the present application and is incorporated herein by reference in its entirety.

Patent application Ser. No. 07/862,950, issued as U.S. Pat. No. 5,315,234, entitled An Eddy Current Device for Inspecting a Component Having a Flexible Support with a Plural Sensor Array, by George H. Sutton, Jr., et al., which discloses and claims a mechanical apparatus for supporting and deploying an eddy current array circuit to substantially conform to a surface of a workpiece being scanned by the apparatus to inspect the workpiece for defects. This patent is also assigned to the same assignee as the present application and is incorporated herein by reference in its entirety.

Patent application Ser. No. 08/125,469, issued as U.S. Pat. No. 5,442,286, entitled Eddy Current Array Inspection Device, by George H. Sutton, Jr., et al, which discloses and claims a device for inspecting a component having a complex geometric shape, such as a dovetail slot, gear tooth or the like using a multiplicity of eddy current probe or circuit elements formed in an array to detect flaws or defects. This patent is also assigned to the same assignee as the present application and is incorporated herein by reference in its entirety.

TECHNICAL FIELD

The present invention relates to the inspection of components using eddy current technology and, more particularly, to a device for inspecting a component such as a round or shaped hole of a gas turbine engine or similar workpiece using a multiplicity of eddy current probe or circuit elements formed in an array.

BACKGROUND OF THE INVENTION

Eddy current inspection is a commonly used technique for detecting discontinuities or flaws in the surface of components of a gas turbine engine. Eddy current techniques are based on the principle of electromagnetic induction in which eddy currents are induced within the component under inspection. The eddy currents are induced in the component by alternating magnetic fields created in a coil of an eddy current probe, referred to as a drive coil, when the probe is moved into proximity with the component under inspection. Changes in the flow of eddy currents are caused by the presence of a discontinuity or a crack in the test specimen. The altered eddy currents produce a secondary magnetic field which is received by the eddy current probe coil or a separate sense coil in the eddy current probe which converts the altered secondary magnetic field to an electrical signal which may be recorded on a strip chart or similar device for analysis. An eddy current machine operator may then detect and size flaws by monitoring and analyzing the recorded signals. Flaws or defects are detected if the electrical signal exceeds a predetermined voltage threshold.

One problem with inspecting components is that the components can contain closed surfaces, such as round or shaped holes, which have heretofore required approximately six hours of labor time per part to inspect for flaws and/or defects. State of the art single coil inspection mode, depending on the area to be inspected, can require as many as thirty passes through the same hole for adequate inspection, taking as long as 4 minutes per area.

It would be desirable, then, to be able to provide capability for the rapid inspection of closed surfaces, such as round or shaped holes, using an inspection device which includes an eddy current array circuit, which is not subject to the foregoing disadvantages. The objects, features and advantages of the present invention will become more readily apparent in the following description when taken in conjunction with the appended drawings.

SUMMARY OF THE INVENTION

The present invention provides a device for inspecting a component, such as a closed surface area of a gas turbine engine or the like, using an eddy current array circuit. The eddy current inspection device of the present invention provides capability for the rapid inspection of any closed surface feature similar to holes of any shape, diameter or depth, in a single pass through the shaped area.

In accordance with the present invention, a device for inspecting a component comprises an eddy current array circuit having an active face for positioning on a surface portion of the component during an inspection operation. A backing is disposed on a face of the eddy current array circuit opposite the active face for applying a uniform pressure behind the array circuit to maintain the array circuit against the surface portion during the inspection operation. An expandable probe tip has exterior side edges and an operating face shaped to cause the eddy current array circuit to conform to the shape of the component under inspection. The eddy current array circuit and the backing are disposed over the operating face with the array circuit active face being closest to the component surface portion and the expandable probe tip having a slot formed therein. The slot has interior sides which narrow toward the operating face at a predetermined slope. The expanding pin with angled sides is provided for respectively matingly engaging the interior sides of the slot to cause the exterior side edges of the expandable probe tip to expand outwardly when the pin is pushed deeper into the slot. An actuator pushes the pin deeper into the slot. Finally, means are provided for electrically connecting the eddy current array circuit to an eddy current instrument.

In the drawings as hereinafter described, a preferred embodiment is depicted; however, various other modifications and alternative constructions can be made thereto without departing from the true spirit and scope of the invention.

BRIEF DESCRIPTION OF THE DRAWINGS

The novel features of the invention are set forth with particularity in the appended claims. The invention itself, however, both as to organization and method of operation, together with objects and advantages thereof, may best be understood by reference to the following description taken in conjunction with the accompanying drawings in which:

DETAILED DESCRIPTION OF THE INVENTION

The present invention will be described with respect to inspecting a shaped aperture of a rotating part of a gas turbine engine component; those skilled in the art, however, will recognize that the principles of the present invention could be easily adapted or modified to inspect any component having a simple or complex geometric surface.

Figure 1A:
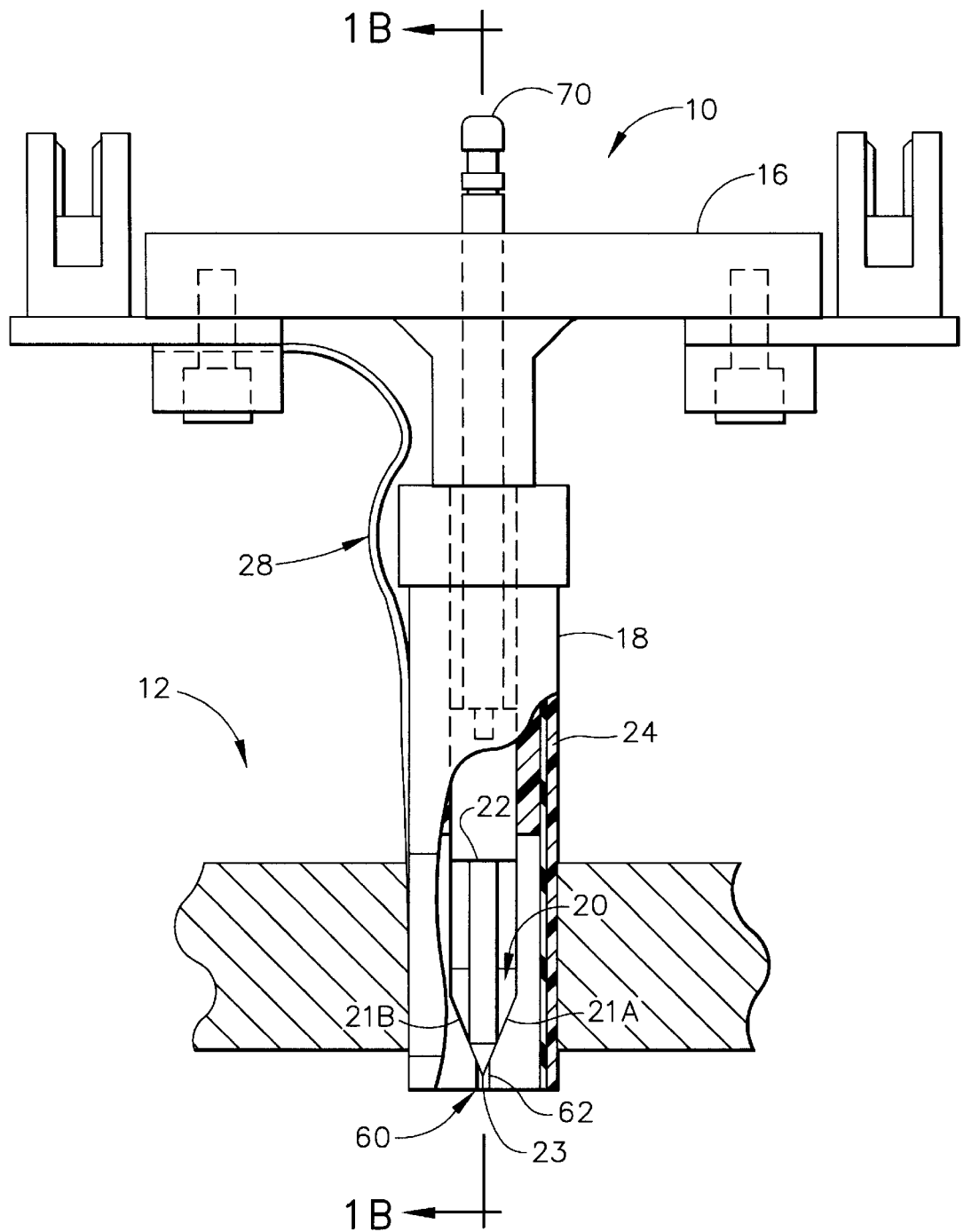
FIG. 1A is a cross-sectional view of an eddy current array inspection device in accordance with the present invention in a non-operative position to facilitate insertion into and removal from a closed surface area, such as a shaped hole, of a gas turbine engine component.

Referring initially to FIG. 1A, the eddy current array probe device 10 for inspecting a closed surface, such as a shaped aperture 12 of a gas turbine engine or the like, includes a probe body base 16 and a probe extension member 18 extending substantially perpendicular to the probe body base 16. An expandable probe tip 20 is positioned at an end 22 of the probe extension member 18 and is movable between a retracted position proximate to the extension member 18 and an inspection position at a spacing from the extension member 18. Referring still to FIG. 1A, the expandable probe tip 20 has expandable exterior side edges 21a and 21b and an operating face 23 shaped to cause an eddy current array circuit to conform to the shape of the component surface under inspection.

Figure 1B:
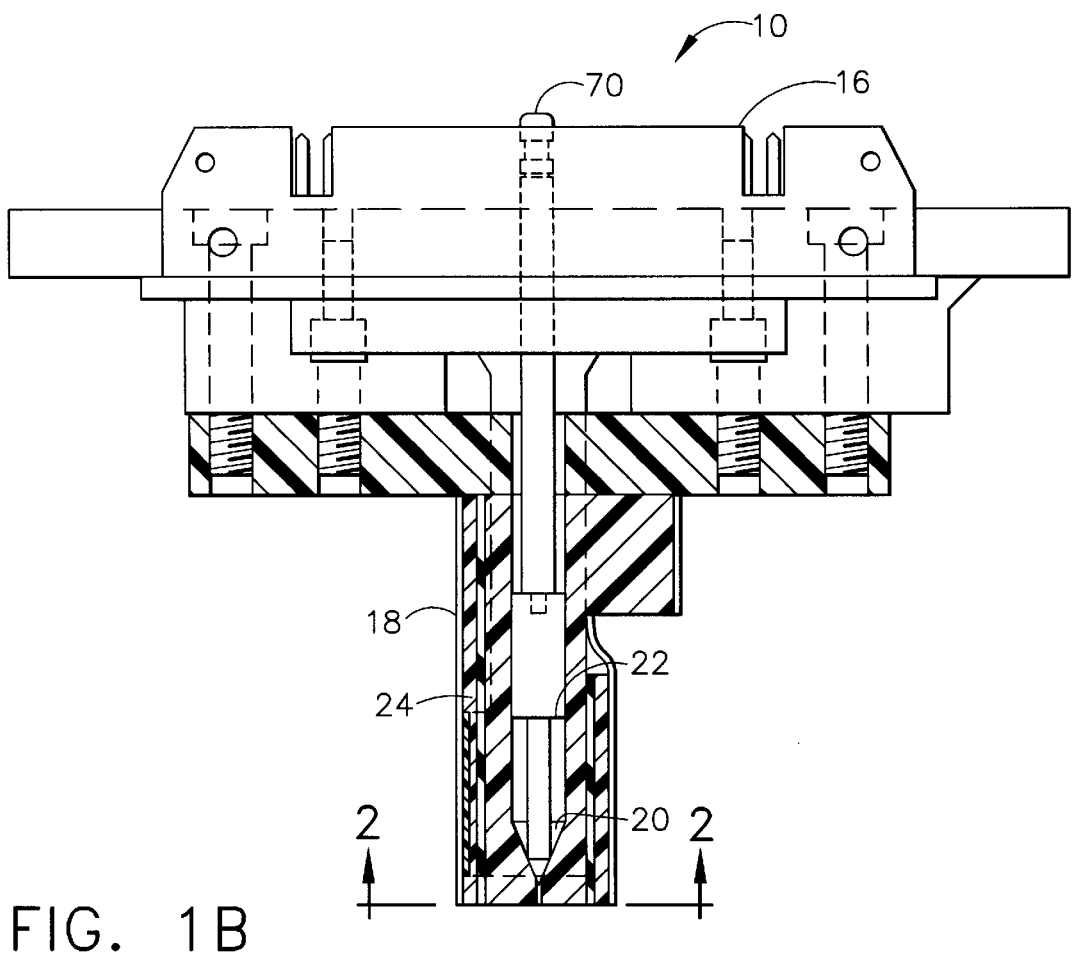
FIG. 1B is a cross-sectional view of the eddy current array inspection device of FIG. 1A in its operative position for scanning along a surface of the shaped hole of a gas turbine engine.
Figure 2:
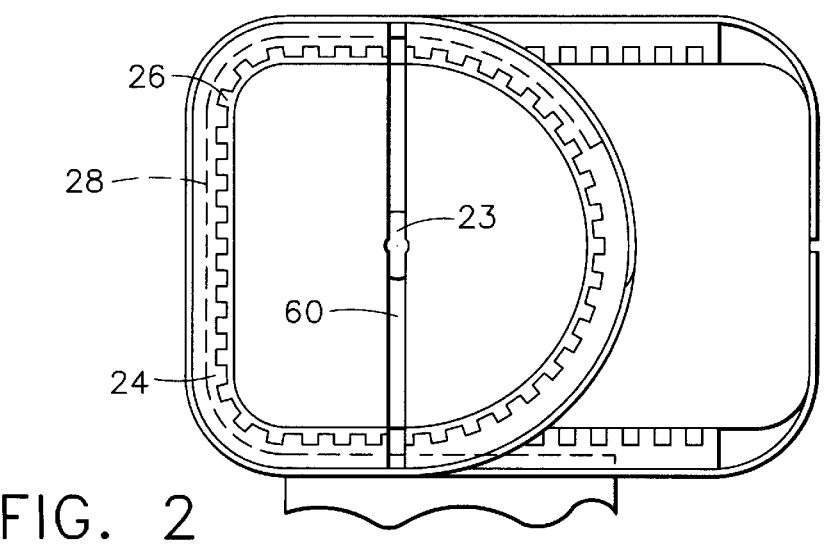
FIG. 2 is a top elevational view of the expandable probe tip of the eddy current array probe device of the present invention.

Continuing with FIG. 1A and referring also to FIG. 1B, a flexible, compliant backing layer 24 and a flexible, compliant eddy current array circuit 28, disposed over the backing layer 24, are both disposed over the operating face 23 and the expandable side edges 21a and 21b of the expandable pin 20 and extend within the interior of the probe extension member 18 to secure the backing 24 and the eddy current array circuit 28 over the expandable pin 20. The backing layer 24 may be made of a ferrite-containing material to concentrate an electromagnetic flux from the drive coils of the eddy current array circuit 28 into the component when each of the drive coils are energized. The compliant backing 24 may have a plurality of ridges 26 formed thereon, which extend substantially parallel to the longitudinal extent of the expandable probe tip and parallel to the intended direction of scan across the inspection surface, to facilitate disposition of the compliant backing 24 over the expandable pin 20 and to permit the compliant backing 24 to conform to any surface under inspection. The ridges 26 also provide support to prevent the backing 24 from lifting off the surface under inspection as the probe body 16 is moved in the direction parallel to the ridges 26 along the surface for inspection thereof.

Eddy current array technology for fast inspection of irregular surfaces is based on high-precision, flexible arrays of sensors used with multiplexing, multi-channel electronics. In prior implementations, the surface has been open, so that there have been essentially no constraints on how to cover the inspection surface area or how to bring out the electronic leads. However, the present invention deals with the inspection of closed surfaces, such as small, shaped bolt holes, where serious constraints exist on how to simultaneously place sensors on the surface and bring out electronic leads without mutual interference.

Figure 3A:
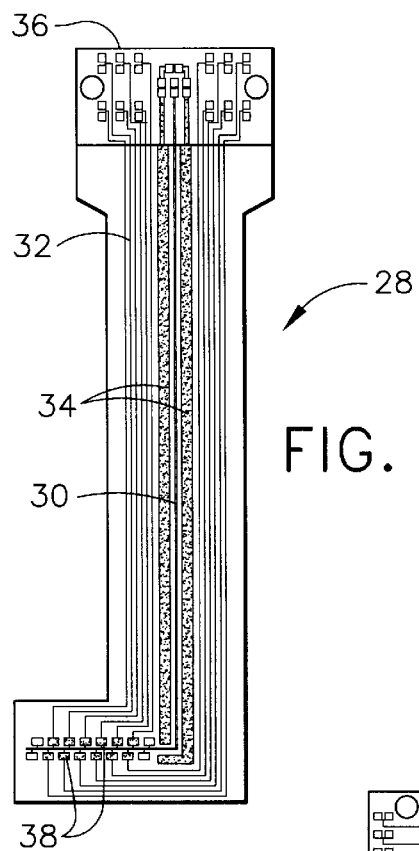
FIGS. 3A and 3B are schematic diagrams illustrating embodiments of an eddy current array circuit sensor configuration in accordance with the present invention.

The eddy current array inspection device of the present invention, therefore, further comprises an improved array sensor that can completely cover a closed surface and, at the same time, bring out electronic leads, thereby enabling fast inspection of closed surfaces. To accomplish this, the present invention proposes an L-shaped sensor/lead configuration 28 as illustrated in FIG. 3A. The L-shaped configuration and sensor 38 arrangement of FIG. 3A allows for the inspection of the complete closed surface with approximately two scans with sensors, or a partial surface with a single scan. Alternatively, sensors 38 may be staggered to completely cover the surface in a single scan, as illustrated in FIG. 3B.

Figure 3B:
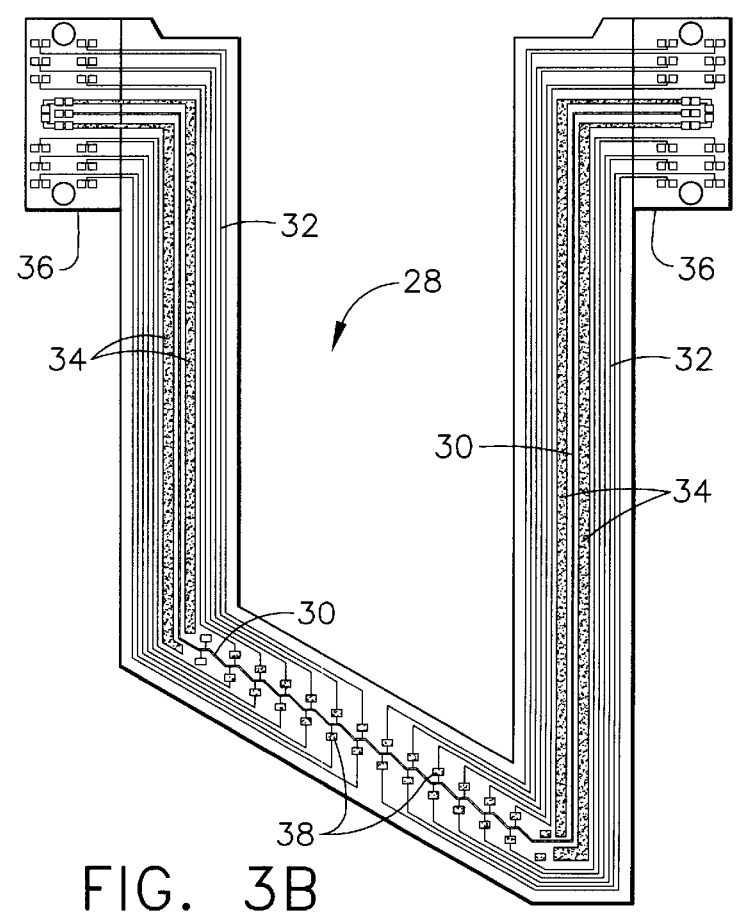

In FIGS. 3A and 3B, the eddy current array circuit 28 includes drive lines 30 and sense lines 32, separated by shielding 34. Of course, those skilled in the art will recognize that the drive and sense lines may be disposed one above the other in different flexible layers or substrates, or configured to reside in the same layer or substrate. The arrangement is connected to an eddy current instrument and connector pads 36. The device 10 comprises means for registering the eddy current array circuit relative to the expandable pin to provide accurate location and size information of any detected defect during an inspection operation.

Referring back to FIGS. 1A and 1B, the eddy current array circuit 28 of FIG. 1A has an active face for positioning against the component surface portion, in this case the interior of the shaped hole 12, during an inspection operation. A compressible layer of moldable material, such as RTV as manufactured by Dow Corning, may be disposed between the backing layer 24, as seen in FIG. 1B, and the expandable probe tip 20 to facilitate compliance or a close uniform fit between the eddy current array circuit 28, in FIG. 1A, and the surface under inspection, and to maintain the drive coils and the sense coils at a respective substantially constant, touching, distance from the component surface portion during scanning by the probe device 10 of FIG. 1A to thereby prevent the adverse effects of lift-off.

In accordance with the present invention, the expandable pin 20 has a slot 60 formed therein with the slot 60 having interior sides 62 which narrow toward the operating face 23 of the expandable pin 20. Referring to FIG. 1A, the main slot 60 may be bifurcated on each end to form narrower longitudinal slots 60. These bifurcated slots permit the opposite exterior side edges 21a and 21b of the expandable pin 20 to expand, to provide conformance between the eddy current array circuit 28 and the surface under inspection. It should also be noted that the interior side edges 62 of the main slot 60 narrow toward the operating face 23 at a predetermined slope.

An expanding pin 20 is disposed partially within the slot 60 and is formed with angled side edges 21a and 21b which are angled at a selected slope to respectively matingly engage the interior sides 62 of the slot 60 to cause the exterior side edges 21a and 21b of the expandable probe tip 20 to expand outwardly when the pin 20 is pushed deeper into the slot 60. The expandable pin 20 is preferably made from a hard insulative material, engineering plastic, such as Delrin®, or the like to prevent interference with the eddy current signals.

The pin 20 is connected to a pin portion 70, which is a portion of expandable pin 20, extending up through a channel formed in the probe body extension member 18, shown in FIG. 1B, and the probe body base 16. The pin 70 is coupled to an actuator (not shown) which applies a force to pin 70 to push the pin 20 further into the slot 60 formed in the expandable pin 20 to cause the sides 21a and 21b of the expandable pin 20 to expand farther and to cause the array circuit 28 to conform to the surface under inspection, as shown in FIG. 12. The actuator may be any suitable device for extending and retracting pin 70.

In operation, the expandable pin 20 is extended from the probe extension member 18 by additional pin portions, similar to pin portion 70 and parallel therewith, and the actuator. The additional pin portions, all integral with expandable pin 20, are coupled to the pin portion 70 by receipt holes or vias. Accordingly, after the array probe device 16 is positioned within a shaped hole 12 for inspection, the actuator may be activated to cause the expandable probe tip 20 to extend from the probe extension member 18 of FIG. 1B and engage the shaped hole 12, as in FIG. 1A, forcing the eddy current array circuit 28 into conformance therewith. This also causes exterior side edges 21a and 21b into contact against the interior walls of the shaped hole 12 to provide compliance between the eddy current array circuit 28 and the side walls of hole 12 for substantially complete inspection of the hole as the probe device 16 in FIG. 1B is moved or scanned along the hole 12.

Those skilled in the art will, therefore, recognize that the present invention provides a novel device for inspecting closed surface areas of a gas turbine engine component or the like in a single scanning operation which prevents the problem of lift-off and provides a device which can be scanned across the closed surface area and easily moved from one closed surface area to another for efficient inspection of shaped holes normally found in rotating parts of a gas turbine engine.

While preferred embodiments of the present invention have been shown and described herein, it will be obvious to those skilled in the art that such embodiments are provided by way of example only. Numerous variations, changes, and substitutions will now occur to those skilled in the art without departing from the invention and those skilled in the art will recognize that the principles of the present invention could be easily adapted or modified to inspect any component having a simple or complex geometric surface. Accordingly, it is intended that the invention be limited only by the spirit and scope of the appended claims.

We claim:

1. A device for inspecting a component comprises:

an eddy current array circuit having an active face for positioning on a surface portion of the component during an inspection operation;

a backing disposed on a face of said eddy current array circuit opposite to said active face for applying a uniform pressure behind said array circuit to maintain the array circuit against the surface portion during the inspection operation;

an expandable pin having exterior side edges and an operating face shaped to cause the eddy current array circuit to conform to the shape of the component under inspection, said eddy current array circuit and said backing being disposed over said operating face with said array circuit active face being closest to the component surface portion and said expandable pin having a slot formed therein, the slot having interior sides which narrow toward said operating face at a predetermined slope, the expanding pin having angled sides for respectively matingly engaging said interior sides of said slot to cause said exterior side edges of said expandable pin to expand outwardly when said pin is pushed deeper into said slot;

an actuator to push said pin deeper into said slot; and means for electrically connecting said eddy current array circuit to an eddy current instrument.

2. The device of claim 1, further comprising means for registering said eddy current array circuit relative to said expandable pin to provide accurate location and size information of any detected defect during an inspection operation.

3. The device of claim 1, further comprising a layer of compressible material disposed between said backing and said expandable pin to provide a close uniform fit between said eddy current array circuit and the closed surface of the component under inspection.

4. The device of claim 1, wherein said eddy current array circuit comprises an L-shaped eddy current array circuit.

5. The device of claim 4, wherein said eddy current array circuit further comprises a plurality of array sensors.

6. The device of claim 5, wherein said plurality of array sensors are arranged in a staggered configuration.

\* \* \* \* \*